(12) United States Patent
Wey

(10) Patent No.: US 11,534,275 B2
(45) Date of Patent: Dec. 27, 2022

(54) METHOD FOR CONSTRUCTING A RESTORATION

(71) Applicant: DENTSPLY SIRONA inc., York, PA (US)

(72) Inventor: Peter Wey, Würenlos (CH)

(73) Assignee: DENTSPLY SIRONA INC., York, PA (US)

( * ) Notice: Subject to any disclaimer, the term of this patent is extended or adjusted under 35 U.S.C. 154(b) by 391 days.

(21) Appl. No.: 16/490,712

(22) PCT Filed: Mar. 2, 2018

(86) PCT No.: PCT/EP2018/055145
§ 371 (c)(1),
(2) Date: Sep. 3, 2019

(87) PCT Pub. No.: WO2018/158411
PCT Pub. Date: Sep. 7, 2018

(65) Prior Publication Data
US 2020/0000562 A1   Jan. 2, 2020

(30) Foreign Application Priority Data
Mar. 3, 2017 (DE) .......................... 102017203475.0

(51) Int. Cl.
*A61C 13/00* (2006.01)
*A61C 9/00* (2006.01)
(Continued)

(52) U.S. Cl.
CPC ........ *A61C 13/0004* (2013.01); *A61C 9/0046* (2013.01); *A61C 13/34* (2013.01);
(Continued)

(58) Field of Classification Search
CPC ..... A61C 13/0004; A61C 13/34; A61C 13/08; A61C 13/082; A61C 9/0046; A61C 19/10; G06N 3/02; G06N 20/10
(Continued)

(56) References Cited

U.S. PATENT DOCUMENTS 10,413,385 B2 *   9/2019   Sherwood ................ A61C 7/00
2006/0210951 A1 * 9/2006   Levanoni ........... A61C 13/0004
                                                                        433/213

(Continued)

FOREIGN PATENT DOCUMENTS

KR   1020110086035 A   7/2011
KR   1020140005337 A   1/2014
(Continued)

OTHER PUBLICATIONS

Raith, S. et al; "Artificial Neural Networks as a powerful numerical tool to classify specific features of a tooth based on 3D scan data."; Computers in Biology and Medicine 80 (2017) 65-76.
(Continued)

*Primary Examiner* — Matthew M Nelson
(74) *Attorney, Agent, or Firm* — Dentsply Sirona Inc.

(57) ABSTRACT

The invention relates to a method for constructing a restoration, in which a dental situation is measured by means of a dental camera and a 3D model of the dental situation is generated. In this case, a computer-assisted detection algorithm is applied to the 3D model of the dental situation, wherein a type of restoration and/or at least a tooth number and/or a position of the restoration to be inserted are automatically determined.

10 Claims, 2 Drawing Sheets

(51) Int. Cl.
  *A61C 13/34* (2006.01)
  *G06N 3/02* (2006.01)
  *G06N 20/10* (2019.01)
  *A61C 13/08* (2006.01)
  *A61C 19/10* (2006.01)

(52) U.S. Cl.
  CPC .............. *G06N 3/02* (2013.01); *A61C 13/082* (2013.01); *A61C 19/10* (2013.01); *G06N 20/10* (2019.01)

(58) Field of Classification Search
  USPC ........................................................ 433/213
  See application file for complete search history.

(56) References Cited

U.S. PATENT DOCUMENTS

| | | | | |
|---|---|---|---|---|
| 2012/0239364 | A1* | 9/2012 | Glor | A61C 1/084 703/11 |
| 2013/0179126 | A1* | 7/2013 | Meier | G06F 30/00 703/1 |
| 2013/0244197 | A1* | 9/2013 | Tjioe | G01J 3/0264 433/29 |
| 2014/0037180 | A1* | 2/2014 | Wang | A61B 6/5217 382/132 |
| 2015/0006465 | A1* | 1/2015 | Mah | A61B 5/0088 706/52 |
| 2015/0056576 | A1* | 2/2015 | Nikolskiy | A61C 13/0004 433/214 |
| 2015/0351870 | A1* | 12/2015 | Mah | A61B 5/0088 600/408 |
| 2016/0224690 | A1* | 8/2016 | Lee | G16H 20/40 |
| 2016/0239784 | A1* | 8/2016 | Selberis | G06Q 10/063114 |
| 2016/0317263 | A9* | 11/2016 | Morales | A61C 8/0089 |
| 2017/0071706 | A1* | 3/2017 | Lee | A61C 13/0004 |
| 2017/0086943 | A1* | 3/2017 | Mah | A61C 9/0053 |
| 2017/0100208 | A1* | 4/2017 | Wen | G06F 30/00 |
| 2017/0249418 | A1* | 8/2017 | Sager | G16Z 99/00 |
| 2017/0273763 | A1* | 9/2017 | Fisker | A61C 9/0046 |
| 2017/0300613 | A1* | 10/2017 | Sager | A61C 13/09 |
| 2018/0071062 | A1* | 3/2018 | Kirchner | A61C 13/0006 |

FOREIGN PATENT DOCUMENTS

| | | |
|---|---|---|
| KR | 101597268 B1 | 2/2016 |
| WO | 9815234 A1 | 4/1998 |
| WO | 2018022752 A1 | 2/2018 |
| WO | 2018158411 A1 | 9/2018 |

OTHER PUBLICATIONS

Miki, Y. et al; "Classification of teeth in cone-beam CT using deep convolutional neural network."; Computers in Biology and Medicine 80 (2017) 24-29.

International Search Report; PCT/EP2018/055145; May 22, 2018 (completed); dated May 30, 2018 (mailed).

Written Opinion of the International Searching Authority; PCT/EP2018/055145; May 22, 2018 (completed); dated May 30, 2018 (mailed).

International Preliminary Report on Patentability; PCT/EP2018/055145; May 22, 2018 (completed); dated May 30, 2018 mailed).

Jayasumana, S. et. al.; "Semantic Image Segmentation with Deep Learning"; Torr Vision Group, Engineering Department, University of Oxford; Jul. 10, 2015; pp. 1-48.

* cited by examiner

METHOD FOR CONSTRUCTING A RESTORATION

TECHNICAL FIELD

The invention relates to a method for constructing a restoration, in which a dental situation is measured by means of a dental camera and a 3D model of the dental situation is generated.

BACKGROUND OF THE INVENTION

A number of methods for planning restorations are known from the state of the art, wherein the user has to manually determine the type of restoration and indicate the tooth number of the restoration to be produced.

One disadvantage of said method is that the user can select an incorrect type of tooth or an incorrect tooth number for the restoration to be produced, so that faulty restorations can result.

The object of the present invention is therefore to provide a method that can determine the type of tooth and/or the tooth number of the restoration to be produced automatically.

SUMMARY OF THE INVENTION

The invention relates to a method for constructing a restoration, in which a dental situation is measured by means of a dental camera and a 3D model of the dental situation is generated. A computer-assisted detection algorithm is applied to the 3D model of the dental situation, wherein a type of restoration and/or at least a tooth number and/or a position of the restoration to be inserted are automatically determined.

The restoration can be any restoration that can, for example, be produced by means of a CAD/CAM method. The dental camera can be any three-dimensional dental camera that, for example, is based on a fringe projection method or a confocal measuring method. The dental situation can include the immediate surroundings of the restoration to be inserted, or a larger area around the restoration to be inserted. The measurement using the dental camera can be carried out from a variety of directions, such as an occlusal direction, a lingual direction, a buccal direction or a labial direction. The 3D model of the dental situation is generated following the measurement by means of the dental camera. The detection algorithm is then applied to the 3D model of the dental situation. The detection algorithm can be based on an artificial neural network for machine learning, for example, or on a template matching procedure. After the analysis of the 3D model by the detection algorithm, the type of restoration and/or the tooth number of the at least one tooth are automatically determined for the restoration to be inserted.

One advantage of this method is that the determination of the type of restoration and the tooth number occurs automatically, without user interaction. This prevents potential operating errors by the user and reduces the amount of time required to plan a restoration.

The type of restoration can advantageously be an inlay, a crown, a bridge, an abutment, a pontic or a veneer.

The bridge can be affixed to the jaw bone using implants and abutments, for example, or can be affixed to the tooth stumps of the adjacent healthy teeth. The bridge can be fixed or removable. The bridge can also be a base bridge that consists of a metal alloy base and a ceramic or plastic upper part.

An abutment is a support post, which serves as a connecting piece between a dental implant and a restoration, such as a crown. An abutment can be releasably or fixedly attached to the implant. Implant abutments can be classified according to the method of production. A distinction is made between prefabricated, custom castable or overpressable, and CAD/CAM implant abutments. Prefabricated abutments are available in different sizes, shapes and angulations, and as grindable or non-grindable varieties. One-piece implants have integrated abutments. Abutments produced using a CAD/CAM method can be customized to the specific dental situation, both with respect to the axis inclination and with respect to the design. Tooth-colored abutments are used in aesthetic restorations, in particular in the area of the front teeth, so as to emulate the optical impression of a natural tooth as much as possible. Abutments are typically made of titanium or a ceramic.

A veneer is a layer of a thin, transparent ceramic shell, in particular for the front teeth.

An inlay is an inlay filling that is placed into a preparation of a tooth. Unlike a plastic filling material, that is introduced into the tooth in soft consistency via shaping aids and subsequently hardened, the inlay is a custom-made work piece that is adhesively bonded into the preparation of the tooth.

A pontic is a bridge that is adhesively bonded onto tooth stumps of healthy adjacent teeth or onto implant abutments. The 3D model of the dental situation is thus analyzed by means of the detection algorithm, in order to select one of said types of restorations.

The dental situation can advantageously comprise at least one preparation or an implant-supported mesostructure, such as an abutment, for placing the restoration to be produced.

A mesostructure, such as an abutment, serves as a connecting element between an implant and a restoration, such as a dental crown, for example. On the basis of the shape of the preparation, a suitable restoration, such as an inlay, a crown, a pontic or a veneer can be constructed.

The restoration to be produced is thus adhesively bonded into the preparation in an accurately fitting manner. The 3D model of the dental situation can thus include a preparation or an abutment.

The computer-assisted detection algorithm can advantageously comprise an artificial neural network for machine learning (convolutional neural network: CNN), wherein the shape of the preparation or the implant-supported mesostructure is analyzed using the 3D model of the dental situation and a suitable type of restoration is selected.

An artificial neural network for machine learning (CNN) is a computer algorithm that allows the automatic identification of the type of restoration. A method using a CNN will be discussed in the following.

A convolutional neural network (CNN) is a feedforward artificial neural network. It is a concept in the field of machine learning that is inspired by biological processes.

Convolutional neural networks are used in numerous modern artificial intelligence technologies, especially for the machine processing of image or audio data.

The structure of a classical CNN generally consists of a convolutional layer followed by a pooling layer. In principle, this unit can be repeated as often as desired.

With a sufficient number of repetitions, they are referred to as deep convolutional neural networks which fall into the area of deep learning.

CNNs learn by learning free parameters or classifiers of convolution kernels per layer and the weighting thereof for the offset to the next layer.

In the first step, the 3D model of the dental situation is recorded with the aid of the dental camera. The recording can take place from an occlusal direction, a lingual direction and/or a labial direction. The position of the restoration to be inserted is determined in the second step. This can be done manually by the user, for example, in that the user selects the position of the restoration to be inserted in a graphical display of the 3D model of the dental situation. The position of the restoration to be inserted can also be determined automatically, by identifying the recording direction and the center of the recording region. The position of the restoration to be inserted then corresponds to a position to which the dental camera points during the measurement.

In a further step, an analysis is carried out in a region of the restoration to be inserted, which can include a preparation, whereby, from various directions, such as an occlusal direction, a mesial direction, a lingual direction, a buccal direction and/or a labial direction, the 3D model of the dental situation is cut into multiple layers, so-called heightfields.

Alternatively to the formation of multiple layers of the 3D model, the heightfields of the 3D model can also be formed by the fact that the brightness of each pixel of a heightfield corresponds to the distance between a respective surface point of the 3D model and a defined position of a virtual camera. Such a heightfield from an occlusal direction would then, for example, contain dark regions, which correspond to surface regions of the 3D model that are disposed further away from the camera, and contain bright regions, which correspond to surface areas of the 3D model that are disposed closer to the camera.

The heightfields of the 3D model are used as the input for a machine learning system, which has been trained using a collection of a large number of 3D models of different dental situations.

In a further step, the 3D model of the dental situation is analyzed by means of the machine learning system and a suitable type of restoration and/or a tooth number of the restoration to be inserted is suggested as the output.

Later in the method, a 3D model of the restoration to be inserted can be calculated on the basis of the known 3D model of the dental situation, including the shape of the preparation, on the basis of the determined type of restoration, and on the basis of the determined tooth number of the restorations to be used. In doing so, an edge of the preparation can be identified automatically and structures, such as adjacent teeth, opposing teeth, and the shape of the preparation can be taken into account. The construction of the restoration can be carried out fully automatically.

In the next step, the restoration can be fully automatically produced from a blank by means of a CAM grinding machine using the constructed 3D model of restoration. The discussed method therefore has the advantage that the restoration can be produced fully automatically without user interaction.

The machine learning system can consist of one or more CNNs.

Color information of the dental situation can also be used as the input for the CNN. The color information is then assigned to the surface points of the 3D model of the dental situation.

The method for training or parameterizing the machine learning system consisting of one or more CNNs will be discussed in the following. A large number of known 3D models of dental situations having a known type of restoration and a known tooth number are analyzed in the first step. Potential input data is generated. The input data is generated in such a way that all possible degrees of freedom are present in the input data. This is achieved by using data augmentation. To do this, the 3D models of the dental situations are rotated about the defined degrees of freedom and/or scaled along the degrees of freedom.

The individual CNNs are then applied to the individual 3D data of the individual 3D models of the dental situations, in order to train the CNNs.

With this method, therefore, the CNNs automatically learn a number of 3D models of dental situations having an already known type of restoration and tooth number with the aid of a training set.

As an alternative to the use of CNNs, an alternative method from the machine learning/deep learning field on the basis of deep belief networks, in which heightfields are likewise used as input data, can be used as well.

A further alternative could be the use of a hybrid method for analyzing the 3D model of the dental situation, whereby classifiers are manually defined by a user, whereby the parameters of the defined classifiers are trained by means of the training set consisting of a large number of known 3D models of a number of dental situations.

The advantage of a CNN, however, is that the parameter values of the internal convolution filters and the further processing of the filter outputs are learned during the analysis of the training set too, as a result of which no further user specification is needed.

The classifiers or characteristics are thus defined automatically and refined during the analysis of the training set. The automatically identified classifiers of a 3D model of a dental situation could be, for example, an entire surface of a preparation or the profile of the edge of the preparation.

The CNN can consist of multiple layers, for example, whereby simple classifiers, such as edges, flat surfaces or regions of the same brightness, can-automatically be identified in a first layer. In a second layer, the classifiers are automatically refined. The classifiers in the second layer can, for example, be the relative arrangement of the edges with respect to one another, the relative direction of the edges or the profile of the edges. The classifiers are increasingly refined in the further layers, as a result of which they become ever more complex. In this way, on the basis of the 3D model as the input parameter, the CNN autonomously learns to automatically determine the suitable type of restoration and/or the tooth number as the output parameter.

Using a surface of at least one residual tooth of the respective tooth, the tooth number and/or a position of the tooth can advantageously additionally be determined for the restoration to be inserted and/or the adjacent teeth relative to the respective tooth.

The tooth number or the position of the tooth is thus determined automatically on the basis of the surface of the residual tooth and/or the adjacent teeth. This is because the detection algorithm automatically identifies what the tooth number of the restoration to be produced is on the basis of the shape, the dimensions and the orientation of the adjacent teeth.

The computer-assisted detection algorithm can advantageously comprise a template matching procedure having defined geometric shapes such as a cusp tip, an incisal edge or a labial surface, wherein, using a surface of at least one residual tooth of the respective tooth, the tooth number and/or a position of the tooth are determined for the restoration to be inserted and/or the adjacent teeth relative to the respective tooth.

This embodiment represents an alternative to the fully automatic machine learning system consisting of at least one CNN. The geometric shapes or characteristics of the 3D model of the dental situation are thus manually defined and parameterized by a user. Therefore, in the template matching procedure, the 3D model of the dental situation to be analyzed is searched for said defined geometric forms. A search algorithm for a cusp tip could, for example, be based on a gradient method. The search algorithm can thus identify and segment distinctive geometric shapes, such as cusp tips, the incisal edge or the labial surface. In this way the tooth number is determined. This is because cuspids can be identified on the basis of the distinctive cusp tips, for example.

The determined type of restoration and/or tooth number can advantageously be displayed to a user with the aid of a display device.

The recorded 3D model of the dental situation can thus be displayed with the aid of a display device such as a monitor, whereby the determined information, such as the type of restoration and/or the tooth number, can be superimposed. The restoration can also be constructed and graphically displayed within the measured 3D model of the dental situation.

The determined type of restoration and/or tooth number can advantageously be used to construct the restoration.

The restoration is consequently constructed fully automatically using the measured 3D model of the dental situation, the determined type of restoration and the tooth number, whereby distinctive structures such as the edge of the preparation, the shape of the preparation, the shape of the adjacent teeth and the shape of the opposing teeth are taken into account.

A fully automatic construction of the restoration without user interaction is thus made possible.

Color information of the residual tooth of the respective tooth can advantageously be used for the restoration to be inserted and/or for the adjacent teeth, in order to define a color for the restoration to be inserted.

The color of the restoration to be inserted can thus be defined automatically by the computer without any user interaction. As a result, the amount of time required for the construction of the restoration is reduced. This also prevents operating errors which, with a manual selection of the color, could lead to a faulty restoration.

The determined type of restoration and/or tooth number can advantageously be used to define a material for the restoration to be produced.

The material for the restoration to be produced is thus also defined automatically by a computer. If the restoration is produced by means of a CAD/CAM production method, a suitable blank made of a suitable material can automatically be selected. The amount of time required for producing a restoration is thus reduced.

BRIEF DESCRIPTION OF THE DRAWINGS

The invention is explained with reference to the drawings. The drawings show.

DETAILED DESCRIPTION OF THE INVENTION

Figure 1:
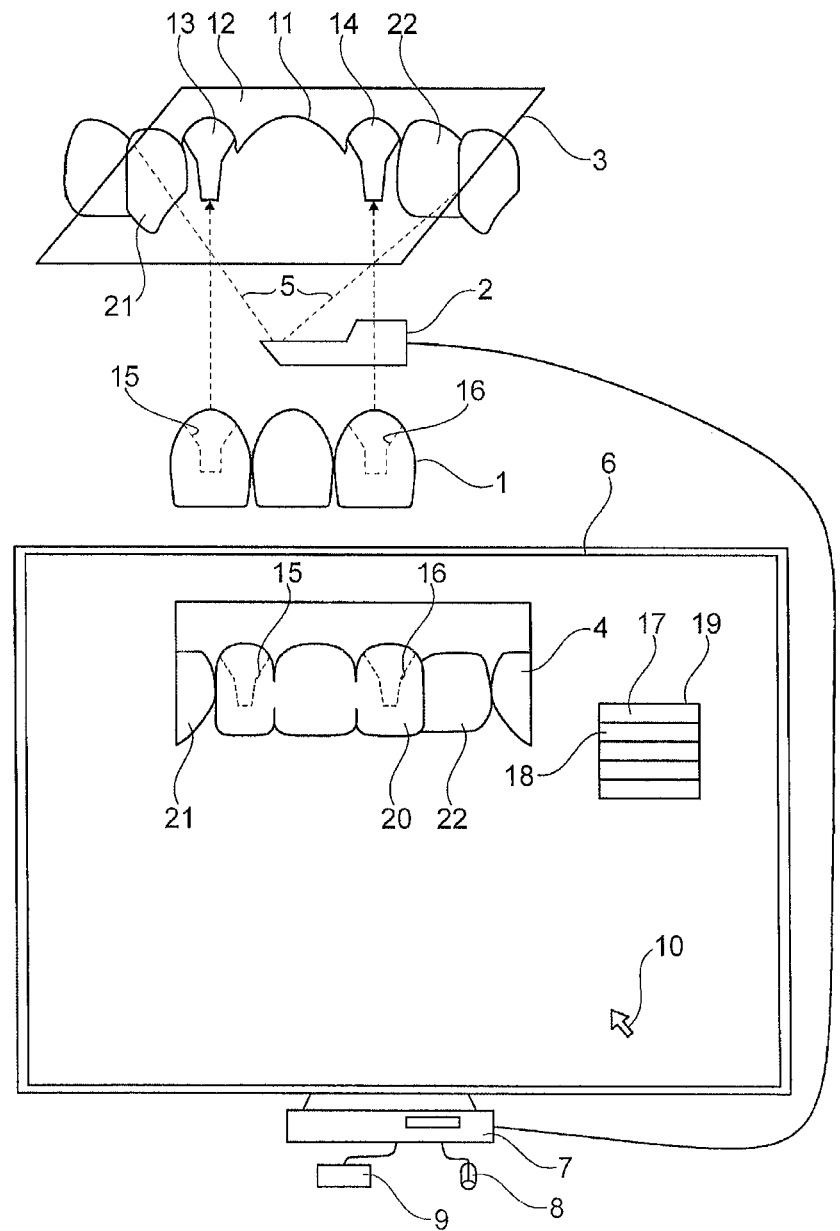
FIG. 1 a sketch for illustrating the method for constructing a restoration.

FIG. 1 shows a sketch for illustrating the method for constructing a restoration 1, such as a bridge, in which a dental situation 3 is measured by means of a dental camera 2 and a 3D model 4 of the dental situation 3 is generated. The measurement of the dental situation 3, which is indicated by a rectangle, by means of the dental camera 2 is indicated by the dashed lines 5. The 3D model 4 of the dental situation 3 is displayed by means of a display device 6, such as a monitor, which is connected to a computer 7. The image data of the three-dimensional camera 2 are forwarded to the computer 7. Input devices such as a mouse 8 and keyboard 9 are connected to the computer 7, so that a user can navigate within the graphical display of the 3D model 4 with the aid of a cursor 10. The dental situation 3 includes a missing incisor 11 of the upper jaw 12 with a tooth number 11 in accordance with the dental chart. A first preparation 13 of the adjacent tooth with the tooth number 12 in accordance with the dental chart is arranged next to it. A second preparation 14 in the form of a tooth stump of the adjacent tooth with the tooth number 21 is arranged on the right side. The restoration 1 to be constructed and produced is shaped such that a first recess 15 is made to fit the first preparation 13 and a second recess 16 is made to fit the second preparation 14. The restoration 1 is thus placed onto the two preparations 13 and 14 and adhesively bonded. Using a computer-assisted detection algorithm, the 3D model 4 of the dental situation 3 is analyzed and a type of restoration 17 and a tooth number 18 are determined automatically, whereby the type of restoration 17 and the tooth number 18 are displayed in a menu 19 by the display device 6. A 3D model 20 of the restoration 1 to be produced is generated automatically on the basis of the measured 3D model 4 of the dental situation 3, the determined type of restoration 17 and the determined tooth number or position of the restoration 18 to be inserted, whereby significant structures, such as the shape of the preparation 15 and the preparation 16, the shape of a first adjacent tooth 21 and a second adjacent tooth 22, are taken into account. The first adjacent tooth 21 is a cuspid having the tooth number 13 and the second adjacent tooth 22 is a tooth having the tooth number 22 in accordance with the dental chart. Using the constructed 3D model 20, the restoration 1 can be carved out of a blank fully automatically by means of a CAM processing machine. The advantage of the discussed method is thus that the restoration 1 can be produced fully automatically after the measurement by means of the dental camera 2, without any need for user interaction.

Figure 2:
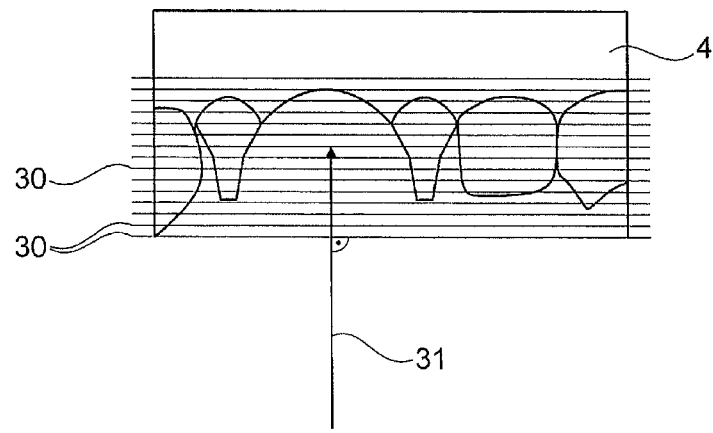
FIG. 2 a sketch for explaining the heightfields in occlusal direction.

FIG. 2 shows a sketch for explaining the heightfields 30 which serve as input data for a CNN, whereby the CNN is a computer algorithm running on the computer 7 of FIG. 1. The 3D model 4 is cut at equal intervals perpendicular to an occlusal direction 31, such that sectional images or heightfields 30 are generated. When training a CNN, a large number of different 3D models of different dental situations are analyzed.

Figure 3:
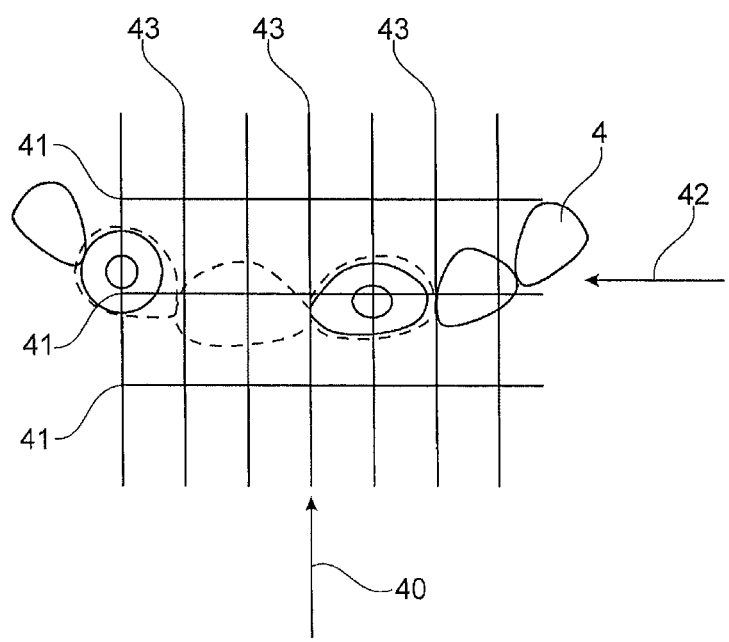
FIG. 3 a sketch for explaining the heightfields in labial and mesial direction.

In FIG. 3, the 3D model 4 is cut perpendicular to a labial direction 40, such that heightfields 41 or sectional images perpendicular to the labial direction 40 are produced. The 3D model 4 is also cut perpendicular to a mesial direction 42 such that height images 43 perpendicular to the mesial direction 42 are produced. The sectional images or height images 30, 41 and 43 serve as input data for the CNN, whereby the type of restoration 17 and the tooth number 18, for example, of the restoration 1 to be inserted of FIG. 1 are determined as output data of the CNN.

REFERENCE SIGNS

1 Restoration
 2 Camera
 3 Dental situation
 4 3D model
 5 Lines of the recording region
 6 Display device
 7 Computer
 8 Mouse
 9 Keyboard
10 Cursor
11 Incisor
12 Upper jaw
13 Preparation
14 Second preparation
15 Recess
16 Second recess
17 Type of restoration
18 Tooth number of restoration to be inserted
19 Menu
20 3D model
21 Adjacent tooth
22 Second adjacent tooth
30 Heightfields
31 Occlusal direction
40 Labial direction
41 Heightfields
42 Mesial direction
43 Height image

The invention claimed is:

1. A method comprising the steps of:
measuring by a dental camera a dental situation;
automatically generating a 3D model of the dental situation from the measured dental situation;
applying to the 3D model of the dental situation, responsive to the generating, and without user interaction after said generating, a computer-assisted detection algorithm to automatically determine, a type of restoration to be inserted into the dental situation;
wherein the dental situation has at least one preparation or an implant-supported mesostructure for inserting the restoration to be produced, wherein the computer-assisted detection algorithm has an artificial neural network for machine learning, and
wherein, based on the 3D model of the dental situation, a shape of the preparation or of the implant-supported in mesostructure is analyzed by a machine learning system and said type of restoration is selected, wherein the machine learning system comprises one or more convolutional neural networks (CNN).

2. The method according to claim 1, wherein the type of restoration is an inlay, a crown, a bridge, an abutment, a pontic or a veneer.

3. The method according to claim 1, wherein using a surface of at least one residual tooth of a respective tooth corresponding to the restoration and/or of adjacent teeth relative to the respective tooth, the tooth number and/or a position of the tooth are additionally determined for the restoration to be inserted.

4. The method according to claim 3, wherein color information of the residual tooth of the respective tooth and/or of the adjacent teeth is used for the restoration to be inserted to specify a color for the restoration to be inserted.

5. The method according to claim 3, wherein the tooth number is determined and the determined type of restoration and/or the tooth number are used to specify a material for the restoration to be produced.

6. The method according to claim 1, wherein the determined type of restoration and/or tooth number are displayed to a user with the aid of a display device.

7. The method according to claim 1, wherein the determined type of restoration and/or tooth number are used to construct the restoration.

8. The method according to claim 1, wherein a machine learning system is trained by generating input data through analyzing a plurality of known 3D models of dental situations having a known type of restoration and a known tooth number;
and augmenting the plurality of known 3D models by rotating said plurality of 3D models about defined degrees of freedom and/or scaling said plurality of 3D models along said degrees of freedom.

9. The method according to claim 8, wherein an individual CNN is applied to an individual 3D data of an individual 3D model of the plurality of known 3D models to train said individual CNN.

10. The method according to claim 1, further comprising:
generating a plurality of heightfields of the 3D model of the dental situation for use as input to said machine learning system.

* * * * *